US00PP23331P2

(12) United States Plant Patent
Hurd

(10) Patent No.: US PP23,331 P2
(45) Date of Patent: Jan. 15, 2013

(54) ***DIANTHUS* PLANT NAMED 'VERY CHERRY'**

(50) Latin Name: ***Dianthus* hybrid**
Varietal Denomination: Very Cherry

(75) Inventor: Kevin A. Hurd, Chicago, IL (US)

(73) Assignee: Walters Gardens, Inc., Zeeland, MI (US)

( * ) Notice: Subject to any disclaimer, the term of this patent is extended or adjusted under 35 U.S.C. 154(b) by 29 days.

(21) Appl. No.: 13/135,664

(22) Filed: Jul. 12, 2011

(51) Int. Cl.
*A01H 5/00* (2006.01)

(52) U.S. Cl. ..... Plt./278; Plt./272

(58) Field of Classification Search ..... Plt./272, Plt./278

See application file for complete search history.

*Primary Examiner* — Susan McCormick Ewoldt

(57) ABSTRACT

The new and distinct plant cultivar of perennial Carnation or Pinks, *Dianthus* plant named 'Very Cherry' with long-blooming, fragrant, single flowers, having petals that begin black-red with irregular bright red streaks that mature to bright red with burgundy center having a streaked outer margin. *Dianthus* 'Very Cherry' is tolerant of high temperatures and resists center die-out.

1 Drawing Sheet

Botanical denomination: *Dianthus* hybrid.
Cultivar designation: 'Very Cherry'.

BACKGROUND OF THE INVENTION

The present invention relates to the new and distinct cultivar of *Dianthus* or Pinks from the genus *Dianthus* and given the cultivar name 'Very Cherry' formerly known by the breeder code 07-13-19. The new plant was the result of an intentional cross in May of 2007 by Kevin A. Hurd between *Dianthus* 'Cranberry Ice' U.S. Plant Pat. No. 18,342 as the female or seed parent and 'Feuerhexe' (not patented) (also commonly known as 'Fire Witch') as the male or pollen parent. The new hybrid was first isolated from trials at a nursery in Zeeland, Mich. during the summer of 2008. *Dianthus* 'Fire and Ice' has been asexually propagated at the same nursery in Zeeland, Mich. using traditional shoot tip cutting procedures and found to reproduce plants that are identical and exhibit all the characteristics of the original plant.

SUMMARY OF THE INVENTION

The present invention has not been evaluated under all possible environmental conditions. The phenotype may vary with variations in environment including: growing temperature, available sunlight, nutrients, water, etc. without a change in the genotype of the plant. The new plant is distinct from its parents and all other *Dianthus* known to the applicant in the following combined traits:

1. Flat, single, overlapping petals opening to black-red with irregular bright red streaks
2. Flower petals mature to bright red with burgundy center and irregular margin.
3. High heat tolerance while not requiring vernalization to produce flowers
4. Floriferous habit, vigorous growth and excellent habit
5. Compact, fine-textured, blue-green foliage Cultivar Comparison Table

| Cultivar | Flower color | Flower pattern | Flower size | Color Petal margin |
|---|---|---|---|---|
| 'Cranberry Ice' U.S. Plant Pat. No. 18,342 | pink | dark wine edge and rim | 3.3 cm | dark wine margin |
| 'Devon Siskin' U.S. Plant Pat. No. 14,377 (Raspberry Swirl) | red purple | magenta edge with burgundy base and light pink eye | 4.0 cm | magenta margin with white edge |
| 'Devon Xera' U.S. Plant Pat. No. 14,895 (Fire Star) | crimson | crimson eye | 3.0 cm | self |
| 'Feuerhexe' (not patented) | fuchsia pink | solid | 4.0 cm | self |
| 'Fire and Ice' | raspberry | pink flecking and white petal margins | 3.5 cm | white |
| Red Dwarf' U.S. Plant Pat. No. 14,437 (Eastern Star) | red | crimson eye | 3.5 cm | self |
| 'Ruby Sparkles' U.S. application No. 13/134,019 (now abandoned) | magenta red | round deep ruby eye | 4.5 cm | deep rose pink |
| 'Spangled Star' U.S. Plant Pat. No. 13,029 | red | pale pink blotch and eye | 4.0 cm | pale pink |
| 'Strawberry Sorbet' U.S. Plant Pat. No. 18,338 | bright red | light pink | 4.0 cm | light pink to white |
| 'Very Cherry' | black-red | burgundy eye and streaks | 3.5 cm | bright red |
| 'Sangria Splash' U.S. Plant Pat. No. 21,781 | fuchsia pink | crimson ring with pink splashing and center | 3.0 cm | crimson with pink splashing |

-continued

Cultivar Comparison Table

| Cultivar | Petal edge | Petal # | Plant height in flower |
|---|---|---|---|
| 'Cranberry Ice' U.S. Plant Pat. No. 18,342 | moderately serrated | 5 | 20 to 25 cm |
| 'Devon Siskin' U.S. Plant Pat. No. 14,377 (Raspberry Swirl) | very fine serration | 5 | 10 cm |
| 'Devon Xera' U.S. Plant Pat. No. 14,895 (Fire Star) | coarsely serrated | 5 | 15 to 20 cm |
| 'Feuerhexe' (not patented) | deeply serrated | 5 | 10 to 12 cm |
| 'Fire and Ice' | Very fine serrated | 5 | 20 to 25 cm |
| Red Dwarf' U.S. Plant Pat. No. 14,437 (Eastern Star) | rounded serration | 5 | 20 to 25 cm |
| 'Ruby Sparkles' U.S. application No. 13/134,019 (now abandoned) | coarsely serrated | 5 | 15 to 20 cm |
| 'Spangled Star' U.S. Plant Pat. No. 13,029 | minutely serrated | 5 | 17 to 22 cm |
| 'Strawberry Sorbet' PP18338 | moderately serrated | 5 | 15 to 20 cm |
| 'Very Cherry' | finely serrated | 5 | 25 to 30 cm |
| 'Sangria Splash' U.S. Plant Pat. No. 21,781 | variably serrated | 5 | 30 cm |

BRIEF DESCRIPTION OF THE DRAWINGS

The photographs of the new invention demonstrate the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
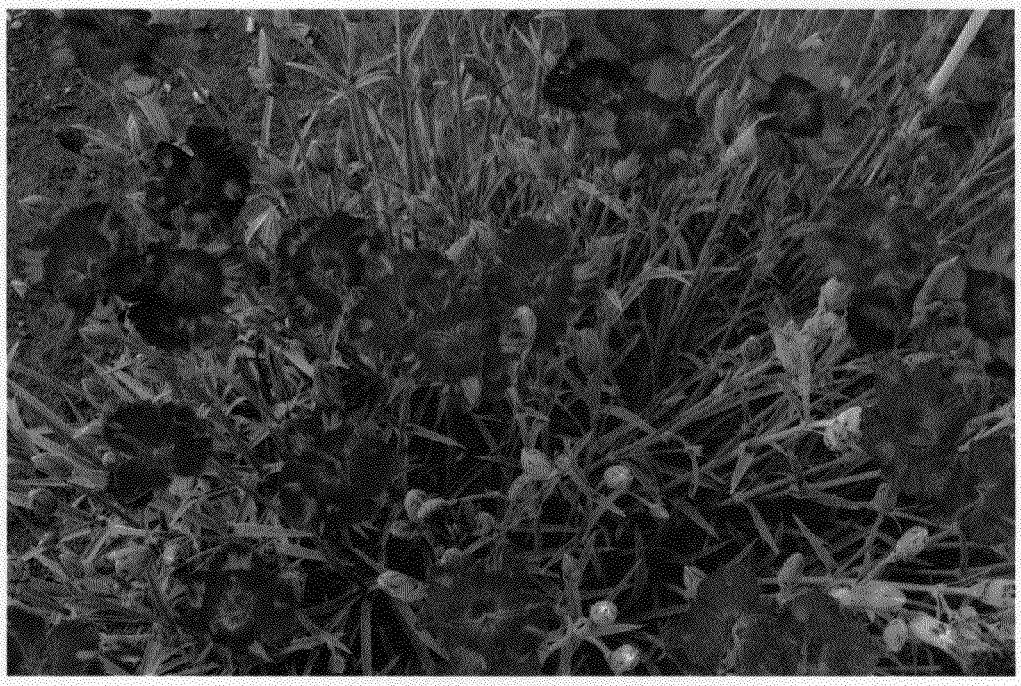
FIG. 1 shows the new plant at two-years of age in a field environment while in flower.
Figure 2:
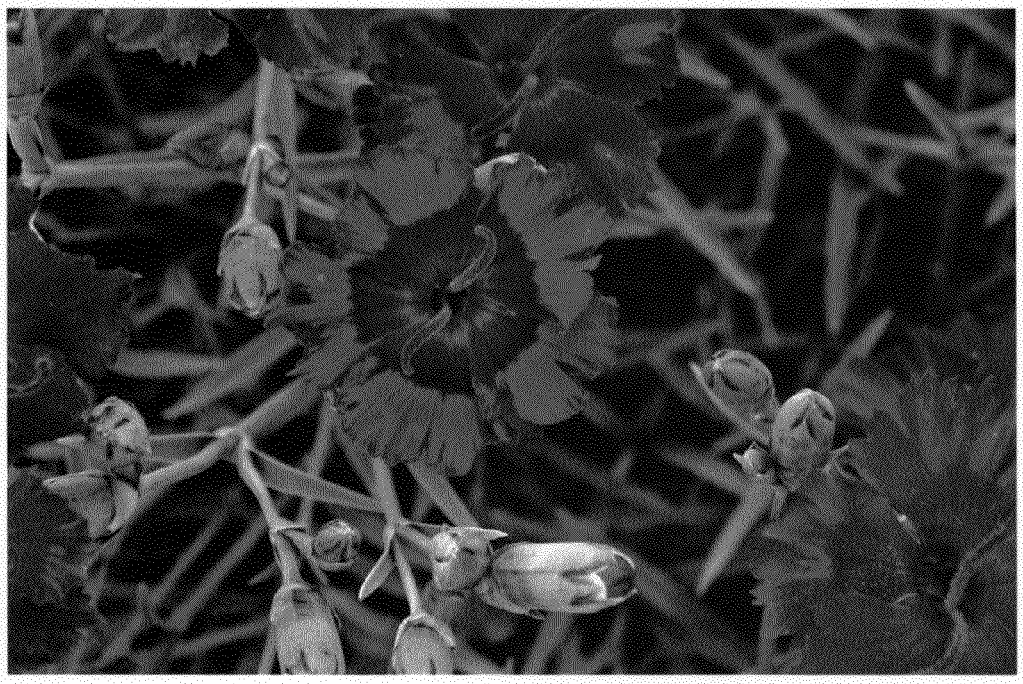
FIG. 2 shows a close-up of the flower and bud.

The following detailed description of the new plant is based on observations of several two-year old plants in open-field, full-sun conditions in Zeeland, Mich. with supplemental watering, light additions of fertilizer and free of other plant growth regulators. All color usage is in reference to the 2001 edition of The Royal Horticultural Colour Chart except where common dictionary terms are used.

Botanical classification: *Dianthus* hybrid.

Parentage: 'Cranberry Ice' as the female or seed parent and 'Feuerhexe' as the male or pollen parent.

Plant description:

*Habit*.—Cespitose, herbaceous, evergreen perennial; stems proximally branched, erect; height of foliage about 15 cm and 42 cm across; height in flower is about 30 cm; Root system; fine, fibrous.

Foliage:

*Leaf type*.—Simple, linear, opposite, decussate, sessile, glabrous, glaucous on adaxial and abaxial; acute apex; base decurrent, adpressed along stem and somewhat perfoliate; no fragrance detected.

*Leaf dimensions*.—About 8.0 cm long and 2.5 mm wide.

*Leaf color*.—More green than RHS 122B and more blue than RHS N138B on adaxial and abaxial sides.

*Venation*.—Minutely reticulate, coloration same as that of leaf top and bottom.

*Stems*.—Mostly erect, terete, glabrous, heavily glaucous, proximally branching at 2 to 3 nodes.

*Stem size*.—To about 30.0 cm long and 3.0 mm wide at base.

*Stem color*.—Nearest RHS 122B.

*Branching*.—Numerous from lower leaf axils; about 180 per plant.

*Nodes*.—3 mm across, nearest RHS 138C.

*Internodes*.—Up to 7.5 cm apart depending on growing temperatures.

Inflorescence:

*Type*.—Terminal, cymose, erect, symmetrical.

*Dimension*.—About 3.5 cm across and extending about 7.0 mm above calyx.

*Flowers per stem*.—3 to 5.

*Pedicel*.—Glaucous, glabrous, terete.

*Pedicel size*.—Variable, 1.5 cm to 3.0 cm long and 2 mm diameter.

*Pedicel color*.—Nearest RHS 122B.

Flowers:

*Type*.—Salverform, single, symmetrical.

*Flower bud shape*.—Rhomboid to terete.

*Flower bud size one day prior to opening*.—About 2.4 cm long and 0.5 cm wide.

*Flower bud color*.—Glaucous, between RHS N138C and RHS 122C; emerging petals nearest RHS 186A.

*Flower period*.—Beginning late May and flowering until frost in the fall with a short 2 week rest after the initial four weeks.

*Flower fragrance*.—Light, sweet spicy, clove-like.

*Flower lasting quality*.—About five days on or off the plant.

*Petals*.—Five; consisting of a rounded blade or limb and a claw enclosed except for 7.0 mm extending above the calyx, limb obovate, apex rounded and dentate with dentations 1.5 mm deep, bearded with minute hairs mostly on the center of the adaxial surface,; petal bent outwardly about 7.0 mm above calyx to nearly a ninety degree angle forming the limb.

*Petal color*.—Petal limb base adaxial side between RHS 46A and RHS 46B with a large center portion with streaked outer margin about 1.6 cm diameter of nearest RHS 53A and a central eye inside of about 5.0 mm of nearest RHS 46A; abaxial side limb nearest RHS 58A; adaxial claw with distal 3.0 mm portion nearest RHS 54D; abaxial claw nearest RHS 145B on a 2.0 mm wide band next to limb and then of near white lighter than RHS 150D on both adaxial and abaxial sides next to limb.

*Dimension*.—3.5 cm long including claw and limb; petal limb to 1.8 cm across and 1.4 cm long; claws about 1.7 cm long and 1.0 mm wide at base and 4.0 mm wide about 3 mm from limb.

*Calyx*.—Glabrous, glaucous, five-toothed corolla tube fused in proximal 1.6 cm; about 2.0 cm long and 6.0 mm in diameter; between RHS N138B and RHS N122B with anthocyanin tinting of nearest RHS 183B on outer abaxial surface and RHS 138B.

*Peduncle*.—Glabrous, glaucous, terete, about 28.0 cm long and 3.0 mm diameter at base; nearest RHS 122B.

*Bracts*.—Two, opposite, glaucous, entire, broadly obtuse with rounded apex, about 5.5 mm long and 4.0 mm wide; between RHS 139A and RHS 139B in the center of both adaxial and abaxial surfaces, lighter than RHS 139D at base and margins.

*Bracteoles*.—Two, opposite and at 90 degrees offset from bracts, oblanceolate, sharply acute apex, bases joined at stem; about 7.0 mm long and 3.0 mm wide; glaucous, entire; between RHS 139A and RHS 139B in the center of both adaxial and abaxial surfaces, lighter than RHS 139D at base and margins.

*Androecium*.—Usually 10 stamens. Filaments: variable in length from 0.7 cm to 2.8 cm long, less than 1 mm diameter; nearest RHS 46A. Anther: elliptic-oblong, dorsifixed; about 3.0 mm long and1.0 mm wide, nearest RHS186D. Pollen; has not yet been observed.

*Gynoecium*.—Style: split in two above ovary. Pistil: about 2.5 cm long and about 1.0 mm diameter; nearest RHS 46A. Stigma: about 1.0 cm long and 1.0 mm wide; curled around nearly 180 degrees at maturity; nearest RHS 53B. Ovary: superior to androecium and inferior to gynoecium, spindle-shaped; about 8.0 mm long and 3.0 mm wide; RHS 145A at distal end and between RHS 145 D and RHS 145 C at proximal end.

Fruit and seed: Production has not yet been observed; calyx between RHS 164A and RHS 164B when dried.

Disease resistance: The new plant is resistance to center die out from fungus or high temperatures. The plant grows best with adequate moisture and well-drained soil, but is able to tolerate high temperatures and some drought once established. Hardiness at least from USDA zone 4 through zone 9.

I claim:

1. A new and distinct plant cultivar of perennial Carnation or Pinks, *Dianthus* plant named 'Very Cherry' as herein described and illustrated, and suitable as a garden ornamental, potted plant and for cut flower arrangements.

* * * * *